United States Patent
Liu et al.

(10) Patent No.: US 9,914,949 B2
(45) Date of Patent: Mar. 13, 2018

(54) **METHOD FOR ENHANCING N-ACETYLGLUCOSAMINE PRODUCTION THROUGH GLCK KNOCKOUT OF *BACILLUS SUBTILIS***

(71) Applicants: Long Liu, Wuxi (CN); Jian Chen, Wuxi (CN); Guocheng Du, Wuxi (CN); Jianghua Li, Wuxi (CN); Yanfeng Liu, Wuxi (CN); Hannes Link, Zurich (CH); Uwe Sauer, Zurich (CH)

(72) Inventors: Long Liu, Wuxi (CN); Jian Chen, Wuxi (CN); Guocheng Du, Wuxi (CN); Jianghua Li, Wuxi (CN); Yanfeng Liu, Wuxi (CN); Hannes Link, Zurich (CH); Uwe Sauer, Zurich (CH)

(73) Assignee: Jiangnan University, Wuxi, JS (CN)

( * ) Notice: Subject to any disclaimer, the term of this patent is extended or adjusted under 35 U.S.C. 154(b) by 18 days.

(21) Appl. No.: 14/934,166

(22) Filed: Nov. 6, 2015

(65) Prior Publication Data

US 2017/0009267 A1  Jan. 12, 2017

(30) Foreign Application Priority Data

Jul. 7, 2015  (CN) .......................... 2015 1 0394205

(51) Int. Cl.
*C12N 15/75* (2006.01)
*C12P 19/26* (2006.01)

(52) U.S. Cl.
CPC .............. *C12P 19/26* (2013.01); *C12N 15/75* (2013.01)

(58) Field of Classification Search
CPC ...... C07K 14/32; C07K 14/524; C12Q 1/689; C12P 19/26; C12P 7/18; C12P 21/00; C12N 15/75; C12N 9/0006; C12N 9/1022; C12N 9/1241; C12N 9/90; C12N 15/74; C12N 1/20; C12N 9/1081; C12N 9/1205; C12N 9/22; A61K 49/00; C12Y 204/99

See application file for complete search history.

(56) References Cited

U.S. PATENT DOCUMENTS

| 2003/0224363 | A1* | 12/2003 | Park ....................... G06F 19/12 435/6.17 |
| 2006/0275905 | A1* | 12/2006 | Bae ........................ A61K 49/00 435/473 |

FOREIGN PATENT DOCUMENTS

| CN | 102978149 A | * | 3/2013 |
| CN | 104498394 A | * | 4/2015 |

* cited by examiner

*Primary Examiner* — Debbie K Ware
(74) *Attorney, Agent, or Firm* — Lili Chen

(57) ABSTRACT

The present invention provides a method for enhancing N-acetylglucosamine production by usage of a recombinant *Bacillus subtilis* with a glcK knockout. This invention enhanced the production of GlcNAc by knocking out the glcK gene which encodes a glucokinase, thus eliminating the GlcNAc phosphorylation to GlcNAc-6-P. The specific growth rate and content of GlcNAc in the supernatant of the recombinant *Bacillus subtilis* with the glcK knockout were 0.15 $h^{-1}$ and 3.0 g/L, respectively, which were 2.32 times and 2.14 times of those of the control strain without glcK knockout. The recombinant *Bacillus subtilis* of the present invention would be potentially useful for industrial production of GlcNAc.

7 Claims, No Drawings

METHOD FOR ENHANCING N-ACETYLGLUCOSAMINE PRODUCTION THROUGH GLCK KNOCKOUT OF BACILLUS SUBTILIS

CROSS-REFERENCES AND RELATED APPLICATIONS

This application claims the benefit of priority to Chinese Application No. 201510394205.7, entitled "A method for enhancing N-acetylglucosamine production through glcK knockout of *Bacillus subtilis*", filed Jul. 7, 2015, which is herein incorporated by reference in its entirety.

BACKGROUND OF THE INVENTION

Field of the Invention

The present invention relates to the field of genetic engineering, and more particularly relates to a method for enhancing N-acetylglucosamine production through glcK knockout of *Bacillus subtilis*.

Description of the Related Art

N-acetylglucosamine (GlcNAc) is a monosaccharide which is widespread in bacteria, yeast, fungi, plants and animals. As a precursor of glycosaminoglycan building blocks, it plays an important role in cartilage and joint health in the human body. Therefore, GlcNAc has long been used as pharmaceuticals and dietary supplements to cure osteroarthritis and maintain cartilage and joint health. In addition, it has wide application in the cosmetic and pharmaceutical fields. Currently, GlcNAc is mainly produced through acid hydrolysis of chitin extracted from crab and shrimp shells; however, this extraction method poses problems such as severe environmental pollution and potential allergic reactions in consumers.

*Bacillus subtilis* (*B. subtilis*) has long been used as a production host for manufacturing pharmaceutically important biochemicals and industrially useful components that meet GRAS grade requirements. Therefore, constructing recombinant *B. subtilis* by metabolic engineering would be an effective strategy to produce GRAS grade GlcNAc.

In previous work, a recombinant *B. subtilis* named BSGN6-$P_{xylA}$-glmS-$P_{43}$-GNA1 was constructed to produce GlcNAc (Ref: Liu, Y. et al. Modular pathway engineering of *Bacillus subtilis* for improved N-acetylglucosamine production. Metab. Eng. 23: 42-52, 2014). And the fermentation medium for GlcNAc production was complex medium, which contained corn steep liquor, yeast extract, tryptone, glucose, etc. However, the stability and controllability of the fermentation process were severely influenced by the complex medium, due to the fact that the compositions of the complex medium in different batches were quite different, especially the corn steep liquor. In addition, the high cost of the complex medium has become a major constraint in industrial production of GlcNAc by recombinant *B. subtilis*. Thus, it would be a great strategy to use synthetic medium for fermentation, which would avoid the differences of the complex medium in different batches and significantly reduce the costs and facilitate the separation and purification of the product. However, experimental data showed that the growth of BSGN6-$P_{xylA}$-glmS-$P_{43}$-GNA1 was slow and the yield of GlcNAc was significantly reduced in the synthetic medium compared to the complex medium. Therefore, it has become an urgent problem to enhance the GlcNAc production of recombinant *B. subtilis* in synthetic media.

The present invention provides a method to enhance the GlcNAc production of recombinant *B. subtilis* in synthetic media and provides other benefits as well.

DETAILED DESCRIPTION

The goal of the present invention is to provide a method for enhancing N-acetylglucosamine production of recombinant *B. subtilis* in synthetic medium. The method is to knock out the glcK gene from the strain BSGN6-$P_{xylA}$-glmS-$P_{43}$-GNA1 and use the recombinant *B. subtilis* thus obtained to produce GlcNAc. The strain BSGN6-$P_{xylA}$-glmS-$P_{43}$-GNA1 is constructed from *B. subtilis* 168 Δ nagP Δ gamP Δ gamA Δ nagA Δ nagB Δ ldh Δ pta::lox72, and the expression of glmS and GNA1 in this strain are under the control of promoter $P_{xylA}$ and $P_{43}$, respectively.

In one embodiment of the present invention, the nucleotide sequence of the glcK which encodes a glucokinase is shown in NCBI with a gene ID: 938206.

In one embodiment of the present invention, the method of constructing the BSGN6-$P_{xylA}$-glmS-$P_{43}$-GNA1 could be referred to a literature (Liu, Y. et al. Modular pathway engineering of *Bacillus subtilis* for improved N-acetylglucosamine production. Metab. Eng. 23: 42-52, 2014).

In one embodiment of the present invention, the GNA1 gene was expressed by the plasmid pP43-GNA1, and the glmS gene was integratively expressed through the plasmid pM7Z6M-$P_{xylA}$-glmS.

In one embodiment of the present invention, the knockout of the glcK gene was achieved by two steps: first, a knockout cassette of glcK gene containing a spectinomycin resistance gene spc was constructed, and then the glcK gene of the BSGN6-$P_{xylA}$-glmS-$P_{43}$-GNA1 was replaced by spc through homologous recombination. The GlcNAc phosphorylation to N-acetylglucosamine-6-phosphate (GlcNAc-6-P) was eliminated through glcK knockout, resulting in increased yield of GlcNAc.

The present invention also provides a recombinant *B. subtilis* with enhanced GlcNAc production in synthetic medium. The recombinant *B. subtilis* was constructed by knocking out the glcK gene of the strain BSGN6-$P_{xylA}$-glmS-$P_{43}$-GNA1. And the BSGN6-$P_{xylA}$-glmS-$P_{43}$-GNA1 was constructed from *B. subtilis* 168 Δ nagP Δ gamP Δ gamA Δ nagA Δ nagB Δ ldh Δ pta::lox72, and the expression of glmS and GNA1 of it were under the control of promoter $P_{xylA}$ and $P_{43}$, respectively.

The present invention also provides a method for producing GlcNAc by the recombinant *B. subtilis* in a synthetic medium containing 20 g/L glucose, 6-8 g/L $Na_2HPO_4$, 1-1.5 g/L $KH_2PO_4$, 2-2.5 g/L $(NH_4)_2SO_4$, 0.2-0.3 g/L $MgSO_4$, 0.5-1.0 g/L $FeSO_4 \cdot 7H_2O$, 0.05-0.1 g/L $MnSO_4 \cdot 4H_2O$, 0.01 g/L thymine and 0.01 g/L tryptophan.

In one embodiment of the present invention, 20 g/L glucose, 7.1 g/L $Na_2HPO_4$, 1.35 g/L $KH_2PO_4$, 2 g/L $(NH_4)_2SO_4$, 0.25 g/L $MgSO_4$, 1.0 g/L $FeSO_4 \cdot 7H_2O$, 0.1 g/L $MnSO_4 \cdot 4H_2O$, 0.01 g/L thymine and 0.01 g/L tryptophan was contained in the synthetic medium.

In one embodiment of the present invention, the method was to transfer the activated seeds of the glcK knockout recombinant *B. subtilis* into the synthetic medium with a inoculum amount of 5%-10% and add xylose as the inducer, and then cultivate the culture for 28-30 hours at 35-37° C. and 200-220 rpm.

Through $^{13}C$ isotope labeling experiments and gene homologous analysis, the inventors found that the glucokinase is a key enzyme of the reverse reaction of GlcNAc biosynthesis, which catalyses the GlcNAc into GlcNAc-6-P.

Therefore, to enhance the production of GlcNAc, the glcK encoding the glucokinase should be knocked out to eliminate the reaction of converting GlcNAc into GlcNAc-6-P.

The recombinant *B. subtilis* with the glcK knockout in the present invention exhibits enhanced GlcNAc production in a synthetic medium, which could reach 3.0 g/L. Although the titer (3.0 g/L) is slightly lower than that of the previous strain BSGN6-$P_{xylA}$-g/mS-$P_{43}$-GNA1 in a complex medium (3.55 g/L), the yield of GlcNAc (150.00 mg/g) is 2.3 times and 1.7 times of those of the BSGN6-$P_{xylA}$-g/mS-$P_{43}$-GNA1 in the synthetic medium (65.00 mg/g) and the complex medium (88.75 mg/g), respectively. In addition, the production of the recombinant *B. subtilis* in the present invention could be further improved by optimizing the components of the medium and the fermentation conditions of fed-batch. The present invention makes a contribution to improve GlcNAc production. And the glcK knockout recombinant *B. subtilis* of the invention has good prospects in industrial production of GlcNAc.

EXAMPLES

Materials and Methods

GlcNAc was detected and quantified by HPLC. The apparatus was agilent 1200 with a differential refraction detector (RID) detector, and the separation column was an $NH_2$ column (250*4.6 mm, 5 m). 70% acetonitrile was used as the mobile phase with a flow rate of 0.75 ml/min. And the column temperature was 30° C., the sample volume was 10 μL.

Seed medium: 10 g/L tryptone, 5 g/L yeast extract, 20 g/L NaCl.

Fermentation medium: a synthetic medium containing 20 g/L glucose, 7.1 g/L $Na_2HPO_4$, 1.35 g/L $KH_2PO_4$, 2 g/L $(NH_4)_2SO_4$, 0.25 g/L $MgSO_4$, 1.0 g/L $FeSO_4.7H_2O$, 0.1 g/L $MnSO_4.4H_2O$, 0.01 g/L thymine and 0.01 g/L tryptophan.

Cultivation conditions: recombinant *B. subtilis* seeds were activated at 37° C., 200 rpm for 12 hours in a seed medium and were transferred into the fermentation medium with a inoculum amount of 5% and xylose was added to the medium to a final concentration of 5 g/L as the inducer, and then the culture was cultivated for 30 hours at 37° C. and 200 rpm.

Example 1

Knockout of the glcK Gene Encoding a Glucokinase

A knockout cassette was constructed based on the front and back sequences of the glcK gene of *B. subtilis* 168 (purchased from the American Type Culture Collection with the ATCC catalog No. 27370) and the sequence of a spectinomycin resistance gene published on NCBI. The nucleotide sequence of the knockout cassette was the same as SEQ ID NO:1.

The knockout cassette was then transformed into the recombinant strain BSGN6-$P_{xylA}$-glmS-$P_{43}$-GNA1, and the recombinant glcK knockout *B. subtilis* named BSGNK was obtained through spectinomycin screening and colony PCR verification. The construction of the BSGN6-$P_{xylA}$-glmS-$P_{43}$-GNA1 could be referred to a periodical literature (Liu, Y. et al. Modular pathway engineering of *Bacillus subtilis* for improved N-acetylglucosamine production. *Metab. Eng.* 23: 42-52, 2014). And the expression of glmS and GNA1 of BSGN6-$P_{xylA}$-glmS-$P_{43}$-GNA1 were under the control of promoter $P_{xylA}$ and $P_{43}$, respectively.

Example 2

Fermentation of GlcNAc by the Recombinant *B. subtilis* BSGNK

Seeds of BSGNK were activated at 37° C., 200 rpm for 12 hours in the seed medium and were transferred into the fermentation medium (a synthetic medium) with an inoculum amount of 5% and xylose was added to the medium to a final concentration of 5 g/L as the inducer, and then the culture was cultivated for 30 hours at 37° C. and 200 rpm.

Results showed that the content of GlcNAc in the supernatant was 3.0 g/L and the specific growth rate of BSGNK was 0.15 $h^{-1}$ in the synthetic medium, which were 2.32 times and 2.14 times of those of the control strain BSGN6-$P_{xylA}$-glmS-$P_{43}$-GNA1, respectively. It indicated that the GlcNAc production of recombinant *B. subtilis* in synthetic medium was enhanced.

Although the titer (3.0 g/L) was slightly lower than that of the previous strain BSGN6-$P_{xylA}$-glmS-$P_{43}$-GNA1 in complex medium (3.55 g/L), the yield (150.00 mg GlcNAc/g glucose) was 2.3 times or 1.7 times of those of the BSGN6-$P_{xylA}$-glmS-$P_{43}$-GNA1 in synthetic medium (65.00 mg/g) or complex medium (88.75 mg/g), respectively. In addition, the production of the recombinant *B. subtilis* in the present invention could be further improved by optimizing the components of the medium and the fermentation conditions of fed-batch. The present invention makes a contribution to improve GlcNAc production. And the obtained recombinant *B. subtilis* has good prospects in industrial production of GlcNAc.

TABLE 1

Fermentation results of BSGN6-$P_{xylA}$-glmS-$P_{43}$-GNA1 in different media

| medium | specific growth rate ($h^{-1}$) | GlcNAc (g/L) | Yield of GlcNAc per glucose (mg/g) |
| --- | --- | --- | --- |
| Complex medium | 0.65 | 3.55 | 88.75 |
| Synthetic medium | 0.07 | 1.3 | 65.00 |

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

<210> 1
<211> 2232
<212> DNA
<213> Artificial sequence for gene knockout

<400> 1
| | | | | | |
|---|---|---|---|---|---|
| cagagcggca | gctgtccttc | gaaaagaatt | ggaacaaaca | aaaaacggaa | gagatttta | 60 |
| taaaggctaa | ggtgataaaa | atggacgaga | tatggtttgc | gggcattgac | ctgggaggaa | 120 |
| cgacgattaa | actcgctttt | attaatcaat | atggcgaaat | tcagcataag | tgggaagttc | 180 |
| cgacagataa | aaccggcgac | acgattactg | tcacaattgc | aaaaacaatc | gacagcaagc | 240 |
| tggatgagct | gcaaaaaccg | aagcacatca | tcaaatacat | cggaatgggt | gcaccaggcc | 300 |
| ctgtagatat | ggcggcagga | gtggtttatg | aaacagtaaa | tctagggtgg | aaaaattatg | 360 |
| ctttgaaaaa | ccatctggag | acagaaaccg | gcatcccagc | tgttatagaa | atgacgcga | 420 |
| atattgctgc | gctcggggaa | atgtggaagg | gagcgggtga | tggcgcaaaa | gacgtcattc | 480 |
| tcgtgacgct | tggcacagga | gttggcggcg | gcatcattgc | aaatggtgaa | attgtacatg | 540 |
| gtataaatgg | cgccggcatc | gattttcgtt | cgtgaataca | tgttataata | actataacta | 600 |
| ataacgtaac | gtgactggca | agagatattt | ttaaaacaat | gaataggttt | acacttactt | 660 |
| tagttttatg | gaaatgaaag | atcatatcat | atataatcta | gaataaaatt | aactaaaata | 720 |
| attattatct | agataaaaaa | tttagaagcc | aatgaaatct | ataaataaac | taaattaagt | 780 |
| ttatttaatt | aacaactatg | gatataaaat | aggtactaat | caaaatagtg | aggaggatat | 840 |
| atttgaatac | atacgaacaa | attaataaag | tgaaaaaaat | acttcggaaa | catttaaaaa | 900 |
| ataaccttat | tggtacttac | atgtttggat | caggagttga | gagtgactaa | aaaccaaata | 960 |
| gtgatcttga | cttttagtc | gtcgtatctg | aaccattgac | agatcaaagt | aaagaaatac | 1020 |
| ttatacaaaa | aattagacct | atttcaaaaa | aaataggaga | taaaagcaac | ttacgatata | 1080 |
| ttgaattaac | aattattatt | cagcaagaaa | tggtaccgtg | gaatcatcct | cccaaacaag | 1140 |
| aatttattta | tggagaatgg | ttacaagagc | tttatgaaca | aggatacatt | cctcagaagg | 1200 |
| aattaaattc | agatttaacc | ataatgcttt | accaagcaaa | acgaaaaaat | aaaagaatat | 1260 |
| acggaaatta | tgacttagag | gaattactac | ctgatattcc | attttctgat | gtgagaagag | 1320 |
| ccattatgga | ttcgtcagag | gaattaatag | ataattatca | ggatgatgaa | accaactcta | 1380 |
| tattaacttt | atgccgtatg | attttaacta | tggacacggg | taaaatcata | ccaaaagata | 1440 |
| ttgcgggaaa | tgcagtggct | gaatcttctc | cattagaaca | tagggagaga | attttgttag | 1500 |
| cagttcgtag | ttatcttgga | gagaatattg | aatggactaa | tgaaatgta | aatttaacta | 1560 |
| taaactattt | aaataacaga | ttaaaaaaat | tataaaaaaa | ttgaaaaaat | ggtggaaaca | 1620 |
| cttttttcaa | ttttttttgtt | ttattattta | atatttggga | aatattcatt | ctaattggta | 1680 |
| atcagatttt | agaaaacaat | aaacccttgc | atatggccgg | cgttatcgga | ggcgcttgga | 1740 |
| tcgctaaaaa | tgaatggctg | aaacatcaaa | attgttaaaa | ttgtgtaaat | gaaattgatt | 1800 |
| ttttgttgtg | ctcaggttaa | gatttaattt | gatgtgttaa | tgagaatgtt | gggaatagac | 1860 |
| tgattttttt | gagcgtgctg | cataggaggt | tgaaatgcga | aaaacgtttt | tttcgaagat | 1920 |
| ttcatttatg | ctgattgcca | ttttattgat | gtggctgaaa | acgtatgctg | tttacaaaac | 1980 |
| cagttttcat | attaaaatcg | acaatctaac | acaggaattt | attctgttta | tcaacccatt | 2040 |
| gagttttttg | ttgcttattt | ttggcctcag | cctgttttta | aaaggcaaaa | acagaaatcg | 2100 |
| ctacattatc | gcgatgagct | gtcttgtcac | gtttgtattg | ctggcaaata | tggttttta | 2160 |
| ccgttttac | aatgatttct | taacaatccc | tgttctttt | caaacgagca | atatgggtga | 2220 |
| tctcggaagc | ag | | | | | 2232 |

SEQUENCE LISTING

<160> NUMBER OF SEQ ID NOS: 1

<210> SEQ ID NO 1
<211> LENGTH: 2232
<212> TYPE: DNA
<213> ORGANISM: artificial sequence
<220> FEATURE:
<223> OTHER INFORMATION: Artificial DNA Sequence for gene Knockout

<400> SEQUENCE: 1

| | | | | | | |
|---|---|---|---|---|---|---|
| cagagcggca | gctgtccttc | gaaaagaatt | ggaacaaaca | aaaaacggaa | gagattttta | 60 |
| taaaggctaa | ggtgataaaa | atggacgaga | tatggtttgc | gggcattgac | ctgggaggaa | 120 |
| cgacgattaa | actcgctttt | attaatcaat | atggcgaaat | tcagcataag | tgggaagttc | 180 |
| cgacagataa | aaccggcgac | acgattactg | tcacaattgc | aaaaacaatc | gacagcaagc | 240 |
| tggatgagct | gcaaaaaccg | aagcacatca | tcaaatacat | cggaatgggt | gcaccaggcc | 300 |
| ctgtagatat | ggcggcagga | gtggtttatg | aaacagtaaa | tctagggtgg | aaaaattatg | 360 |
| ctttgaaaaa | ccatctggag | acagaaaccg | gcatcccagc | tgttatagaa | atgacgcga | 420 |
| atattgctgc | gctcggggaa | atgtggaagg | gagcgggtga | tggcgcaaaa | gacgtcattc | 480 |
| tcgtgacgct | tggcacagga | gttggcggcg | gcatcattgc | aaatggtgaa | attgtacatg | 540 |
| gtataaatgg | cgccggcatc | gattttcgtt | cgtgaataca | tgtttataata | actataacta | 600 |
| ataacgtaac | gtgactggca | agagatattt | ttaaaacaat | gaataggttt | acacttactt | 660 |
| tagttttatg | gaaatgaaag | atcatatcat | atataatcta | gaataaaatt | aactaaaata | 720 |
| attattatct | agataaaaaa | tttagaagcc | aatgaaatct | ataaataaac | taaattaagt | 780 |
| ttatttaatt | aacaactatg | gatataaaat | aggtactaat | caaaatagtg | aggaggatat | 840 |
| atttgaatac | atacgaacaa | attaataaag | tgaaaaaaat | acttcggaaa | catttaaaaa | 900 |
| ataaccttat | tggtacttac | atgtttggat | caggagttga | gagtggacta | aaaccaaata | 960 |
| gtgatcttga | cttttagtc | gtcgtatctg | aaccattgac | agatcaaagt | aaagaaatac | 1020 |
| ttatacaaaa | aattagacct | atttcaaaaa | aaataggaga | taaaagcaac | ttacgatata | 1080 |
| ttgaattaac | aattattatt | cagcaagaaa | tggtaccgtg | gaatcatcct | cccaaacaag | 1140 |
| aatttattta | tggagaatgg | ttacaagagc | tttatgaaca | aggatacatt | cctcagaagg | 1200 |
| aattaaattc | agatttaacc | ataatgcttt | accaagcaaa | acgaaaaaat | aaaagaatat | 1260 |
| acggaaatta | tgacttagag | gaattactac | ctgatattcc | attttctgat | gtgagaagag | 1320 |
| ccattatgga | ttcgtcagag | gaattaatag | ataattatca | ggatgatgaa | accaactcta | 1380 |
| tattaacttt | atgccgtatg | attttaacta | tggacacggg | taaatcata | ccaaaagata | 1440 |
| ttgcgggaaa | tgcagtggct | gaatcttctc | cattagaaca | tagggagaga | attttgttag | 1500 |
| cagttcgtag | ttatcttgga | gagaatattg | aatggactaa | tgaaaatgta | aatttaacta | 1560 |
| taaactattt | aaataacaga | ttaaaaaaat | tataaaaaaa | ttgaaaaaat | ggtggaaaca | 1620 |
| cttttttcaa | ttttttttgtt | ttattattta | atatttggga | aatattcatt | ctaattggta | 1680 |
| atcagatttt | agaaaacaat | aaaccccttgc | atatggccgg | cgttatcgga | ggcgcttgga | 1740 |
| tcgctaaaaa | tgaatggctg | aaacatcaaa | attgttaaaa | ttgtgtaaat | gaaattgatt | 1800 |
| ttttgttgtg | ctcaggttaa | gatttaattt | gatgtgttaa | tgagaatgtt | gggaatagac | 1860 |
| tgatttttt | gagcgtgctg | cataggaggt | tgaaatgcga | aaacgttttt | ttcgaagat | 1920 |
| ttcatttatg | ctgattgcca | ttttattgat | gtggctgaaa | acgtatgctg | tttacaaaac | 1980 |
| cagttttcat | attaaaatcg | acaatctaac | acaggaattt | attctgttta | tcaacccatt | 2040 |

```
gagtttttttg ttgcttattt ttggcctcag cctgttttta aaaggcaaaa acagaaatcg    2100
ctacattatc gcgatgagct gtcttgtcac gtttgtattg ctggcaaata tggttttta     2160 ccgttttttac aatgatttct taacaatccc tgttcttttt caaacgagca atatgggtga    2220
tctcggaagc ag                                                         2232
```

What is claimed is:

1. A recombinant *Bacillus subtilis* with increased GlcNAc production as compared to the parent strain BSGN6-$P_{xylA}$-glmS-$P_{43}$-GNA1, wherein said recombinant *Bacillus subtilis* is constructed by knocking out a glcK gene of the strain BSGN6-$P_{xylA}$-glmS-$P_{43}$-GNA1; wherein said glcK gene encodes a glucokinase; and wherein said BSGN6-$P_{xylA}$-glmS-$P_{43}$-GNA1 is constructed from *Bacillus subtilis* 168 Δ nagP Δ gamP Δ gamA Δ nagA Δ nagB Δ ldh Δ pta::lox72, and the expression of glmS and GNA1 of said BSGN6-$P_{xylA}$-glmS-$P_{43}$-GNA1 are under the control of promoter $P_{xylA}$ and $P_{43}$, respectively.

2. The recombinant *Bacillus subtilis* of claim 1, wherein the nucleotide sequence of said glcK gene has a NCBI gene ID: 938206.

3. The recombinant *Bacillus subtilis* of claim 1, wherein said glcK gene is knocked out by the following steps:
   a) constructing a knockout cassette of said glcK gene containing a spectinomycin resistance gene spc; and
   b) replacing said glcK gene of BSGN6-$P_{xylA}$-glmS-$P_{43}$-GNA1 with said spc gene by transforming said knockout cassette into said BSGN6-$P_{xylA}$-glmS-$P_{43}$-GNA1.

4. A method for production of increased GlcNAc, comprising producing increased GlcNAc by using the recombinant *Bacillus subtilis* of claim 1, wherein said recombinant *Bacillus subtilis* is cultured in a synthetic medium to produce increased GlcNAc; and wherein said synthetic medium contains 20 g/L glucose, 6-8 g/L $Na_2HPO_4$, 1-1.5 g/L $KH_2PO_4$, 2-2.25 g/L $(NH_4)_2SO_4$, 0.2-0.3 g/L $MgSO_4$, 0.5-1.0 g/L $FeSO_4 \cdot 7H_2O$, 0.05-0.01 g/L thymine and 0.01 g/L tryptophan.

5. The method of claim 4, wherein said syntehtic medium contains 20 g/L glucose, 7.1 g/L $Na_2HPO_4$, 1.35 g/L $KH_2PO_4$, 2 g/L $(NH_4)_2SO_4$, 0.25 g/L $MgSO_4$, 1.0 g/L $FeSO_4 \cdot 7H_2O$, 0.01 g/L $MnSO_4 \cdot 4H_2O$, 0.01 g/L thymine and 0.01 g/L tryptophan.

6. The method of claim 4, wherein said method for producing said increased GlcNAc comprises transferring activated seeds of said recombinant *Bacillus subtilis* into said synthetic medium with an inoculum amount of 5%-10% and adding xylose as an inducer; and cultivating for 28-30 hours at 35-37° C. and 200-220 rpm.

7. The method of claim 6, wherein said xylose is added to said synthetic medium to a final concentration of 5 g/L.

* * * * *